(12) United States Patent
Faulhaber et al.

(10) Patent No.: US 11,759,157 B2
(45) Date of Patent: Sep. 19, 2023

(54) HYBRID MEDICAL APPARATUS

(71) Applicant: Siemens Healthcare GmbH, Erlangen (DE)

(72) Inventors: Markus Faulhaber, Möhrendorf (DE);
Hans-Jürgen Müller, Pretzfeld (DE);
Karl Stierstorfer, Erlangen (DE);
Gabriel Haras, Baiersdorf (DE);
Michael Kaus, Nuremberg (DE)

(73) Assignee: Siemens Healthcare GmbH, Erlangen (DE)

( * ) Notice: Subject to any disclaimer, the term of this patent is extended or adjusted under 35 U.S.C. 154(b) by 41 days.

(21) Appl. No.: 17/115,774

(22) Filed: Dec. 8, 2020

(65) Prior Publication Data

US 2021/0177365 A1    Jun. 17, 2021

(30) Foreign Application Priority Data

Dec. 11, 2019   (DE) ..................... 10 2019 219 306.4

(51) Int. Cl.
| | | |
|---|---|---|
| *A61N 5/00* | (2006.01) | |
| *A61B 6/00* | (2006.01) | |
| *A61B 6/04* | (2006.01) | |

(52) U.S. Cl.
CPC .......... *A61B 6/4452* (2013.01); *A61B 6/0407* (2013.01); *A61B 6/4078* (2013.01);
(Continued)

(58) Field of Classification Search
CPC ................................................... A61N 5/1081
See application file for complete search history.

(56) References Cited

U.S. PATENT DOCUMENTS

| | | |
|---|---|---|
| 6,888,919 B2 | 5/2005 | Graf |
| 7,239,684 B2 | 7/2007 | Hara |
| | (Continued) | |

FOREIGN PATENT DOCUMENTS

| | | |
|---|---|---|
| DE | 102007060189 A1 | 2/2009 |
| DE | 102010026674 B4 | 9/2012 |
| | (Continued) | |

OTHER PUBLICATIONS

German Office Action for German Application No. 10 2019 219 306.4 dated Oct. 7, 2020.
(Continued)

*Primary Examiner* — Dani Fox
(74) *Attorney, Agent, or Firm* — Lempia Summerfield Katz LLC

(57) ABSTRACT

A hybrid medical apparatus having an imaging unit, an irradiation unit, and a patient support apparatus is provided. The imaging unit is configured to record image data of an examination region. The irradiation unit is configured to carry out an irradiation of at least a part of the examination region. The imaging unit and the irradiation unit have a common isocenter. The irradiation unit is arranged for rotational movement along a first perimeter independently of the imaging unit. An X-ray source and an X-ray detector of the imaging unit are arranged for movement such that a central beam between the X-ray source and the X-ray detector runs through the common isocenter. The patient support apparatus and/or the imaging unit and/or the irradiation unit is movable along a first spatial axis such that the examination region of the examination object is able to be arranged in the common isocenter.

16 Claims, 10 Drawing Sheets

(52) U.S. Cl.
CPC .......... *A61B 6/4275* (2013.01); *A61B 6/4085* (2013.01); *A61B 6/4405* (2013.01); *A61B 6/4458* (2013.01)

(56) References Cited

U.S. PATENT DOCUMENTS

| | | |
|---|---|---|
| 7,295,648 B2 | 11/2007 | Brown |
| 8,666,021 B2 | 3/2014 | Fadler |
| 8,917,813 B2 | 12/2014 | Maurer, Jr. |
| 9,498,167 B2 | 11/2016 | Mostafavi |
| 9,731,148 B2 | 8/2017 | Olivera |
| 2003/0048868 A1 | 3/2003 | Bailey |
| 2009/0039268 A1 | 2/2009 | Peter |
| 2010/0290586 A1 | 11/2010 | Friedrich |
| 2011/0210261 A1* | 9/2011 | Maurer, Jr. ............ A61B 6/025 250/393 |
| 2012/0165651 A1 | 6/2012 | Yamaya |
| 2012/0177171 A1 | 7/2012 | Gutfleisch |
| 2012/0230464 A1 | 9/2012 | Ling |

FOREIGN PATENT DOCUMENTS

| | | |
|---|---|---|
| DE | 102015210755 A1 | 12/2015 |
| DE | 102009021740 B4 | 12/2018 |
| EP | 1715361 B1 | 2/2015 |
| EP | 2539020 B1 | 3/2017 |
| EP | 2665519 B1 | 12/2017 |

OTHER PUBLICATIONS

Lee, Seung Hyun, et al. "X-band Linac for a 6 MeV dual-head radiation therapy gantry." Nuclear Instruments and Methods in Physics Research Section A: Accelerators, Spectrometers, Detectors and Associated Equipment 852 (2017): 40-45.

* cited by examiner

HYBRID MEDICAL APPARATUS

This application claims the benefit of German Patent Application No. DE 10 2019 219 306.4, filed on Dec. 11, 2019, which is hereby incorporated by reference in its entirety.

BACKGROUND

The present embodiments relate to a hybrid medical apparatus.

With the advance of technology in radiation therapy (e.g., in relation to irradiation precision and/or the power of radiation doses and/or compensation for movement), a precise localization of tissue to be irradiated (e.g., a tumor) is of increasing importance. Where possible, healthy tissue should be protected against irradiation and/or saved in such cases.

For irradiation planning and/or for supervision of an irradiation for an examination object, an imaging modality (e.g., a medical X-ray device and/or a computed tomography system and/or a magnetic resonance system) is used. In such cases, a rearrangement and/or repositioning of the examination object is frequently disadvantageously necessary between the imaging and the irradiation of the examination object. This often results in inaccuracy in the localization of an isocenter of the irradiation in the examination object.

Three-dimensional and high-resolution imaging is further necessary for precise irradiation planning and/or a precise supervision of the irradiation.

SUMMARY AND DESCRIPTION

The scope of the present invention is defined solely by the appended claims and is not affected to any degree by the statements within this summary.

The present embodiments may obviate one or more of the drawbacks or limitations in the related art. For example, an apparatus that is suitable for carrying out an irradiation and for three-dimensional high-resolution imaging of an examination region of an examination object without any rearrangement of the examination object is provided.

Features and advantages mentioned here are able to be transferred between the various forms of embodiment.

In accordance with a variant of an embodiment, the hybrid medical apparatus has an imaging unit, an irradiation unit, and a patient support apparatus. The imaging unit is further configured to record image data of an examination region of an examination object arranged on the patient support apparatus. Moreover, the irradiation unit is configured to carry out an irradiation of at least one part of the examination region of the examination object. In this case, the imaging unit and the irradiation unit have a common isocenter. The irradiation unit is further arranged for rotational movement along a first perimeter independently of the imaging unit. Further, the imaging unit has an X-ray source and an X-ray detector. In this case, the X-ray source and the X-ray detector are arranged so that the X-ray source and the X-ray detector are movable such that a central beam between the X-ray source and the X-ray detector runs through the common isocenter. In this case, the X-ray source emits an X-ray fan beam for recording the image data. The patient support apparatus and/or the imaging unit and/or the irradiation unit are arranged for movement at least along a first spatial axis such that the examination region of the examination object is arrangeable in the common isocenter.

In such cases, the examination object may be a human patient and/or an animal patient and/or a phantom and/or a workpiece, for example. The examination region of the examination object may further include a spatial (e.g., three-dimensional) region that is able to be predetermined by tissue to be irradiated (e.g., a tumor). For example, the examination region may be determined by at least one anatomical feature of the examination object (e.g., a tissue boundary and/or an organ).

In this case, the examination object may be arranged on the patient support apparatus (e.g., on a surface of the patient support apparatus). The patient support apparatus may, for example, include at least one patient support plate, where the examination object may be arranged on the patient support plate. Moreover, the patient support apparatus may include multiple patient support plates, able to be moved adjustably in relation to one another, where the examination object may be arranged differently on the patient support plates. In this case, the examination object may, for example, be arranged lying and/or sitting on the patient support apparatus. In this case, the at least one patient support plate may, for example, be supported by a mobile pedestal and/or by a robot arm. The mobile pedestal and/or the robot arm may further be fastened to the imaging unit and/or the irradiation unit.

The patient support apparatus may further be able to be moved along the first spatial axis (e.g., relative to the imaging unit and/or the irradiation unit), such that the examination region of the examination object arranged on the patient support apparatus may be arranged in the common isocenter.

The imaging unit has an X-ray source and an X-ray detector. The imaging unit is further configured for diagnostic slice imaging (e.g., for diagnostic multislice imaging) of the examination region of the examination object. In this case, the X-ray source may be configured to emit at least one X-ray fan beam. The at least one X-ray fan beam in this case may include multiple part X-ray beams that, starting from the X-ray source, illuminate a spatial slice of the examination region of the examination object. In this case, the multiple part X-ray beams run in parallel to a common central plane of the at least one X-ray fan beam, where the central beam of the X-ray source lies in the common central plane. The part X-ray beams further run at different angles in parallel to the common central plane in relation to the central beam of the X-ray source in each case. For example, the X-ray source may be configured for emitting multiple X-ray fan beams running in parallel to the common central plane in each case.

In one embodiment, the X-ray detector may be configured as a row detector (e.g., as a multi-row detector). In this case, the X-ray detector may further be configured, when struck by the at least one X-ray fan beam, after an interaction with the examination region to be imaged (e.g., of the spatial slice) of the examination object, to provide an X-ray signal. The X-ray detector may further provide an X-ray signal for each of the X-ray fan beams emitted by the X-ray source in each case, which corresponds to one row of the X-ray detector (e.g., the spatial slice of the examination region of the examination object).

In one embodiment, the X-ray source and the X-ray detector are arranged for movement such that the central beam between the X-ray source and the X-ray detector (e.g., a central point of the X-ray detector) always runs through the common isocenter. For this, the X-ray source and the X-ray detector may be arranged for coordinated movement. The X-ray source and the X-ray detector may have the same or different degrees of freedom of movement. The X-ray source and/or the X-ray detector may, for example, each be arranged for rotational movement and/or for translational movement. In this case, the X-ray source and the X-ray detector may be movable in a fixed arrangement or and/or coordinated with one another.

In one embodiment, the X-ray source and the X-ray detector (e.g., the arrangement of X-ray source and X-ray detector) may be arranged for movement such that the examination region of the examination object is illuminatable from different projection directions (e.g., angulations). The recording of multiple X-ray signals from different angulations enables a reconstruction of image data (e.g., in a similar way to a computed tomography) that images the spatial slice of the examination region of the examination object to be made possible. In this case, the reconstruction may include a Radon transformation and/or Fourier transformation. The image data may further be three-dimensional. In this case, the image data may include multiple picture elements (e.g., voxels). In one embodiment, the spatial slice may be reconstructed with an isovoxel resolution.

The irradiation unit may have a ray source that is configured for emitting an ionizing radiation. In this case, the ionizing radiation may be suitable for tumor therapy and/or for killing tumor cells. The ionizing radiation may, for example, further include X-ray radiation and/or Gamma radiation and/or particle radiation (e.g., electron radiation and/or proton radiation and/or ion radiation). In this case, the irradiation unit (e.g., the ray source) may be able to be moved along the first perimeter such that the ionizing radiation is alignable on a center of the irradiation within the examination region of the examination object. In this case, the center of the irradiation corresponds to the common isocenter. The first perimeter may be configured as elliptical (e.g., circular) in this case. In one embodiment, the irradiation unit (e.g., the ray source) may be movable along the first perimeter such that tissue adjoining the examination region of the examination object is not irradiated with the ionizing radiation.

In this case, the irradiation unit may be arranged independently of the imaging unit (e.g., independently of the X-ray source and the X-ray detector) for rotational movement along the first perimeter.

The irradiation unit may have a ring-shaped first gantry, for example, where the examination object arranged on the patient support apparatus is arrangeable in an opening of the first gantry. In this case, the ring-shaped first gantry may have an elliptical (e.g., circular) course. The ray source may further be movable along the first spatial axis (e.g., relative to the patient support apparatus and/or to the examination object arranged thereon).

The imaging unit may further have a ring-shaped second gantry, where the examination object arranged on the patient support apparatus is arrangeable in an opening of the second gantry. In this case, the ring-shaped second gantry may have an elliptical (e.g., circular) course. The imaging unit may further be movable along the first spatial axis (e.g., relative to the patient support apparatus and/or to the examination object arranged thereon).

In this case, the first gantry may be arranged at least partly within the second gantry. As an alternative, the second gantry may be arranged at least partly within the first gantry. In one embodiment, the first gantry and the second gantry are movable at least along the first spatial axis relative to one another. What may be achieved by this is that the irradiation unit and the imaging unit have the common isocenter.

In one embodiment, the hybrid medical apparatus may have a housing that surrounds the imaging unit and the irradiation unit such that both the examination region of the examination object are arranged in the common isocenter and also the imaging unit and the irradiation unit are movable independently along the respective degrees of freedom of movement. This enables the imaging unit and the irradiation unit to be protected against an external mechanical influence and/or contamination and/or an external chemical influence.

In one embodiment, the hybrid medical apparatus may make possible an irradiation and three-dimensional high-resolution slice imaging (e.g., simultaneously) of the examination region of the examination object. In this case, the examination object may remain at rest on the patient support apparatus during the irradiation and slice imaging.

In a further embodiment of the hybrid medical apparatus, the imaging unit may have a further X-ray source and a further X-ray detector. In this case, the further X-ray source and the further X-ray detector may each be arranged movably around the common isocenter such that, in an operating state of the hybrid medical apparatus, a further central beam between the further X-ray source and the further X-ray detector runs at a predetermined angle in relation to the central beam through the common isocenter.

The further X-ray source may, for example, have all characteristics of the X-ray source. The further X-ray detector may further have all characteristics of the X-ray detector.

The further X-ray source may further be configured for emitting at least one further X-ray fan beam. The at least one further X-ray fan beam in this case can include multiple part X-ray beams that, starting from the further X-ray source, illuminate a further spatial slice of the examination region of the examination object. In this case, the multiple part X-ray beams run in parallel to a common central plane of the at least one further X-ray fan beam, where the further central beam of the further X-ray source lies in the common central plane. The part X-ray beams further run at different angles in each case in relation to the further central beam of the further X-ray source in parallel to the common central plane. For example, the further X-ray source may be configured for emitting multiple further X-ray fan beams in each case running in parallel to the common central plane.

In one embodiment, the further X-ray detector may be configured as a row detector (e.g., as a multi-row detector). In this case, the further X-ray detector may further be configured to provide a further X-ray signal on being struck by the at least one further X-ray fan beam, after an interaction with the examination region to be imaged (e.g., the further spatial slice) of the examination object. The further X-ray detector may provide a further X-ray signal in each case for each of the further X-ray fan beams emitted by the further X-ray source, which corresponds to a row of the further X-ray detector (e.g., of the further spatial slice of the examination region of the examination object).

In one embodiment, the further X-ray source and the further X-ray detector are arranged for movement such that the further central beam between the further X-ray source and the further X-ray detector (e.g., a central point of the further X-ray detector) always runs through the common isocenter. For this, the further X-ray source and the further X-ray detector may be arranged to move in a coordinated fashion. The further X-ray source and the further X-ray detector may further have the same or different degrees of freedom of movement. The further X-ray source and/or the further X-ray detector may, for example, be arranged for rotational movement and/or translational movement. In this case, the further X-ray source and the further X-ray detector may be movable in a fixed arrangement and/or coordinated with one another.

In this case, the arrangement including the further X-ray source and the further X-ray detector may be movable such that, in an operating state of the hybrid medical apparatus, the further central beam runs at a predetermined (e.g., temporally constant) angle in relation to the central beam through the common isocenter. This enables a biplanar imaging of the examination region of the examination object by the imaging unit to be made possible.

In a further embodiment of the hybrid medical apparatus, the imaging unit and/or the irradiation unit may be movable tiltably and/or translationally.

In this case, the imaging unit may be movable, for example, tiltably and/or translationally relative to the irradiation unit. The irradiation unit may further be movable tiltably and/or translationally relative to the imaging unit. Moreover, the imaging unit and/or the irradiation unit may be movable tiltably and/or translationally relative to the patient support apparatus (e.g., to the examination object arranged on the patient support apparatus). Further, the imaging unit and the irradiation unit may be movable tiltably and/or translationally in a fixed arrangement to one another in relation to the examination object. In this case, the imaging unit and/or the irradiation unit may be supported movably by at least one hexapod.

This enables an especially flexible adaptation of a positioning of the irradiation unit and/or of the imaging unit in relation to the examination region of the examination object to be made possible. This further enables a change in location of the examination object to be avoided. In this case, the irradiation unit and the imaging unit may be optimally positioned (e.g., individually and/or independently of one another) in accordance with the respective anatomical and/or technical requirements by tilting and/or a translational movement in relation to the examination region of the examination object. In this case, the movement of the irradiation unit and/or the imaging unit may moreover be coordinated tiltably and/or translationally such that any mutual interference between irradiation unit and imaging unit may be minimized during the respective positioning.

This enables an irradiation of tissue adjoining the examination region to be reduced.

In this case, an absolute and/or relative positioning of the imaging unit and/or of the irradiation unit and/or of the patient support apparatus and/or of the examination object (e.g., during the irradiation and/or imaging) may be determined with regard to a spatial coordinate system. In this case, the absolute and/or relative positioning may include information about the spatial position and/or spatial alignment and/or spatial orientation and/or a pose of the imaging unit and/or of the irradiation unit and/or of the patient support apparatus and/or of the examination object. The relative positioning of the imaging unit and/or of the irradiation unit and/or of the patient support apparatus and/or of the examination object in relation to each other may further be determined. For this, the positioning may be determined, for example, in relation to a patient coordinate system and/or a device coordinate system of the imaging unit and/or of the irradiation unit and/or of the patient support apparatus. In this case, the different coordinate systems may be registered with one another.

In one embodiment, the irradiation unit and/or the imaging unit and/or the patient support apparatus may have a movement unit. In this case, the movement unit may include at least a wheel and/or a robot arm and/or a rail system and/or a hexapod. IN one embodiment, the movement unit may make possible a tilting movement and/or a translational movement of the irradiation unit and/or of the imaging unit and/or of the patient support apparatus. In this case, the irradiation unit and/or the imaging unit and/or the patient support apparatus may be movable, for example, relative to a room floor by the movement unit. The movement unit may further be configured for movable mechanical coupling of the irradiation unit and/or of the imaging unit and/or of the patient support apparatus to one another and/or to a mounting facility of a room (e.g., a rail system).

In a further embodiment of the hybrid medical apparatus, the X-ray source and the X-ray detector may be arranged to be movable along a second perimeter. The irradiation by the irradiation unit may be undertaken as a function of a positioning of the imaging unit and/or the recording of the image data from the examination region of the examination object as a function of a positioning of the irradiation unit.

The second perimeter in this case may be configured to be elliptical (e.g., circular). The first perimeter and the second perimeter may further run within a common plane. In this case, the first perimeter may run outside the second perimeter. The second perimeter may further run outside the first perimeter.

Further, the first perimeter may run in a plane that is parallel or not parallel to the plane of the second perimeter (e.g., perpendicular thereto).

This enables a movement of the X-ray source and of the X-ray detector along the second perimeter, and also a movement of the irradiation unit along the first perimeter without the X-ray source and the X-ray detector mechanically obstructing one another.

Where the first perimeter and the second perimeter are configured as circular, a radius of the first perimeter may be greater than a radius of the second perimeter. A radius of the second perimeter may further be greater than a radius of the first perimeter. The first perimeter and the second perimeter may have a common central point (e.g., the common isocenter).

The X-ray source and the X-ray detector may further be arranged movably along the second perimeter such that the central beam between the X-ray source and the detector runs through the common isocenter in each operating state of the hybrid medical apparatus.

In one embodiment, the at least one part of the examination region of the examination object may be irradiated by the irradiation unit as a function of the spatial positioning of the imaging unit (e.g., at that moment). In this case, the spatial positioning of the imaging unit may, for example, include information about the spatial position and/or spatial alignment and/or spatial orientation and/or a pose of the imaging unit (e.g., of the X-ray source and of the X-ray detector). In one embodiment, the irradiation by the irradiation unit may be blocked automatically when a radiopaque component of the imaging unit is arranged in the beam path of the irradiation unit.

The imaging unit, for repeated (e.g., periodic) recording of the image data from the examination region of the examination object, may further carry out multiple rotational passes along the second perimeter. In this case, the irradiation by the irradiation unit may be undertaken as a function of an operating parameter and/or recording parameter of the imaging unit (e.g., pulsed).

Further, the image data from the examination region of the examination object may be recorded as a function of a spatial positioning (e.g., at that moment) of the irradiation unit. This enables image artifacts that may be caused by an arrangement of at least one part of the irradiation apparatus within the beam path of the imaging unit to be avoided.

In one embodiment, the movement and/or positioning of the X-ray source and of the X-ray detector along the second perimeter, the movement and/or positioning of the irradiation unit along the first perimeter, the recording of the image data by the imaging unit, and the irradiation by the irradiation unit may be coordinated.

Where the imaging unit has the further X-ray source and the further X-ray detector, the further X-ray source and the further X-ray detector may be arranged for movement along a third perimeter.

In this case, the third perimeter may be configured as elliptical (e.g., circular). A plane of the third perimeter may be arranged in an operating state of the hybrid medical apparatus (e.g., temporally constant) at the predetermined angle to a plane of the second perimeter. In this case, the plane of the third perimeter and the plane of the second perimeter may each be different from a plane of the first perimeter in an operating state of the hybrid medical apparatus.

In a further embodiment of the hybrid medical apparatus, in an operating state of the hybrid medical apparatus, a plane of the first perimeter may be different than a plane of the second perimeter.

In this case, the plane of the first perimeter may run in parallel or not in parallel (e.g., at right angles) to the plane of the second perimeter. The plane of the first perimeter may further be movable relative to the plane of the second perimeter (e.g., within a predetermined angular range). Similarly, the plane of the second perimeter may be movable relative to the plane of the first perimeter (e.g., within a predetermined angular range).

In this case, the first perimeter and the second perimeter may run nested interdependently and/or not interdependently. For a course of the first perimeter and of the second perimeter nested interdependently, an angular range, within which a collision-free movement of the plane of the first perimeter and/or of the plane of the second perimeter is possible, may be predetermined.

With a non-interdependent course of the first perimeter and of the second perimeter, the plane of the first perimeter and/or the plane of the second perimeter may be moved independently and collision-free in relation to one another.

In one embodiment, the movement of the plane of the first perimeter and/or of the plane of the second perimeter may be as a function of the positioning of the examination object on the patient support apparatus. For example, the plane of the first perimeter and/or of the plane of the second perimeter may be moved without any collisions.

With an elliptical embodiment of the first perimeter and/or of the second perimeter, the examination object (e.g., a longitudinal examination object) may be surrounded by the first perimeter and/or the second perimeter.

The fact that the plane of the first perimeter is different than the plane of the second perimeter in the operating state of the hybrid medical apparatus enables an advantageous positioning of the at least one slice during the recording of the image data in relation to a central beam of the irradiation unit to be made possible. For example, through a movement of the plane of the second perimeter (e.g., during a movement of the arrangement of X-ray source and X-ray detector along the second perimeter), multiple slice images of different angulations (e.g., a three-dimensional volume including multiple spatial slices) may be recorded as image data.

In a further embodiment of the hybrid medical apparatus, in an operating state of the hybrid medical apparatus, the plane of the first perimeter may be able to be moved around the common isocenter. In this case, the irradiation unit may be arranged for movement on a first ellipsoid around the common isocenter.

In this case, the plane of the first perimeter may be tiltable and/or rotatable around the common isocenter in the operating state of the hybrid medical apparatus. The first perimeter may be configured such that the examination object, after arrangement of the examination region in the common isocenter, is able to be surrounded in the three spatial directions at least partly (e.g., completely) by the first perimeter.

With a circular embodiment of the first perimeter, the irradiation unit may be arranged on a first sphere surface as an embodiment of the first ellipsoid for movement around the common isocenter. In this case, a central point of the first perimeter and of the first sphere surface may coincide with the common isocenter.

With an elliptical embodiment of the first perimeter, the irradiation unit may be arranged on the first ellipsoid for movement around the common isocenter. In this case, the first ellipsoid may have different spatial extents in at least two spatial directions. In one embodiment, the elliptically embodied first perimeter may have a large and a small half axis. In this case, the large half axis may be arranged predominantly in parallel to a longitudinal direction of the patient support apparatus (e.g., of the examination object). By comparison with an embodiment as a sphere surface, a spatial extent of the first ellipsoid along the small half axis may further be adapted to an extent of the patient support apparatus (e.g., of the examination object) at right angles to the longitudinal direction.

This enables the examination object to be able to be completely surrounded by the irradiation apparatus in the three spatial directions, where a space requirement of the hybrid medical apparatus may be minimized.

For the movement of the irradiation unit along the first perimeter (e.g., on the first ellipsoid) around the common isocenter, an operating parameter of the irradiation unit may be adapted during the irradiation of the at least one part of the examination region based on the spatial positioning of the irradiation unit at that moment.

This enables an especially flexible and precise irradiation of the at least one part of the examination region of the examination object by the irradiation unit to be made possible.

In this case, the movement of the plane of the first perimeter around the common isocenter may be restricted such that a spatial region around the patient support apparatus and/or the examination object remains open. For example, at least along the small and/or large half axis of the first ellipsoid, an opening for bringing the patient support apparatus and the examination object in and/or out may remain open during the movement of the plane of the first perimeter.

In a further embodiment of the hybrid medical apparatus, the plane of the second perimeter, in an operating state of the hybrid medical apparatus, may be able to be moved around the common isocenter. In this case, the X-ray detector and the X-ray source may be arranged for movement on a second ellipsoid around the isocenter.

In this case, the plane of the second perimeter, in the operating state of the hybrid medical apparatus, may be able to be tilted and/or rotated around the common isocenter. The second perimeter may further be configured such that the examination object, after arrangement of the examination region in the common isocenter, is able to be surrounded at least partly (e.g., completely) in the three spatial directions by the first perimeter.

With a circular embodiment of the second perimeter, the irradiation unit may be arranged for movement on a second sphere surface as an embodiment of the second ellipsoid around the common isocenter. In this case, a central point of the second perimeter and of the second sphere surface may coincide with the common isocenter.

With an elliptical embodiment of the second perimeter, the imaging unit (e.g., the X-ray source and the X-ray detector) may be arranged on the second ellipsoid for movement around the common isocenter. In this case, the second ellipsoid may have different spatial extents in at least two spatial directions. In one embodiment, the elliptically embodied second perimeter may have a large and a small half axis. In this case, the large half axis may be arranged predominantly in parallel to a longitudinal direction of the patient support apparatus (e.g., of the examination object). A spatial extent of the second ellipsoid may be adapted along the small half axis by comparison with an embodiment as sphere surface to an extent of the patient support apparatus (e.g., of the examination object) at right angles to the longitudinal direction.

This enables the examination object to be able to be completely surrounded by the X-ray source in the three spatial directions and to be able to be illuminated by the source with the X-ray fan beam, where a space requirement of the hybrid medical apparatus may be minimized.

With the movement of the imaging unit (e.g., of the X-ray source and of the X-ray detector), along the second perimeter (e.g., on the second ellipsoid), around the common isocenter, an operating parameter and/or recording parameter of the imaging unit during the recording of the image data from the examination region of the examination object may be adapted based on the spatial positioning of the imaging unit at that moment. For example, a fan angle of the X-ray fan beam emitted from the X-ray source may be adapted as a function of the spatial positioning of the X-ray source and/or of the X-ray detector at that moment.

The X-ray source and the X-ray detector may, for example, further be movable (e.g., tiltable) in relation to the second perimeter. What may be achieved by this is that the central beam between the X-ray source and the X-ray detector runs through the common isocenter in each spatial position along the second perimeter (e.g., on the second ellipsoid). In one embodiment, the X-ray source and the X-ray detector, with a movement along the second perimeter, may each be moved coordinated in relation to the second perimeter (e.g., tilted), such that the central beam runs through the common isocenter. In this case, the common isocenter may be different from the focal points of the second ellipsoid. In one embodiment, the common isocenter may lie on the main axis of the second ellipsoid.

This enables an especially flexible three-dimensional imaging of the examination region of the examination object by the imaging unit to be made possible.

In this case, the movement of the plane of the second perimeter around the common isocenter may be restricted such that a spatial region around the patient support apparatus and/or the examination object remains open. For example, an opening for bringing the patient support apparatus and the examination object in and/or out at least along the small and/or large half axis of the second ellipsoid may remain open during the movement of the plane of the second perimeter.

Where the plane of the first perimeter and the plane of the second perimeter, in an operating state of the hybrid medical apparatus, are able to be moved around the common isocenter, the movement may be coordinated. The first ellipsoid may further lie (e.g., completely) within the second ellipsoid. As an alternative, the second ellipsoid may lie (e.g., completely) within the first ellipsoid. In one embodiment, the movement of the plane of the first perimeter and the movement of the plane of the second perimeter around the common isocenter may be restricted such that a spatial region around the patient support apparatus and/or the examination object (e.g., in each operating state of the hybrid medical apparatus) remains open. For example, in each case, an opening for bringing the patient support apparatus and the examination object in and/or out at least along the small and/or large half axis of the first and the second ellipsoid may remain open during the movement of the plane of the first perimeter and the movement of the plane of the second perimeter.

This enables direct access to the examination object and/or rapid removal of the examination object from the hybrid medical apparatus to be provided. The movable arrangement of the irradiation unit on the first ellipsoid and the movable arrangement of the imaging unit on the second ellipsoid further enables an especially space-saving embodiment of the hybrid medical apparatus to be made possible (e.g., at the same time as the greatest possible spatial coverage of the examination object arranged on the patient support apparatus).

In a further embodiment of the hybrid medical apparatus, the irradiation unit may have a first side and a second side in parallel to a plane of the first perimeter. The X-ray detector may further be arranged on the first side, and the X-ray source may further be arranged on the second side of the irradiation unit for rotational movement around a common spatial axis in each case, with the common spatial axis running at right angles to the plane of the first perimeter.

In one embodiment, the X-ray source and the X-ray detector may have a phase displacement of 180° to each other with regard to a rotational movement around the common spatial axis. This enables it to be provided that the central beam runs through the common isocenter. In this case, the common isocenter may lie on or away from the common spatial axis.

The rotationally movable arrangement of the X-ray source and of the X-ray detector each on different sides of the irradiation unit enables a double-cone-shaped sampling (e.g., illumination) of the examination region of the examination object by the imaging unit to be made possible. Any mutual interference between the irradiation unit and the imaging unit may also be excluded by this.

In a further embodiment of the hybrid medical apparatus, the X-ray source and the X-ray detector may be movable in parallel to the common spatial axis relative to one another. In this case, the common spatial axis may run along a longitudinal axis of the patient support apparatus (e.g., of the examination object).

Through a translational movement of the X-ray source relative to the X-ray detector in parallel to the common axis of rotation, a spatial distance between the X-ray source and the X-ray detector may be adapted (e.g., with dynamic timing). This enables the opening angle of the double-cone-shaped sampling of the examination region of the examination object to be adapted. In this case, the double-cone-shaped sampling of the examination region of the examination object by the imaging unit may be adapted, for example, during an irradiation of the at least one part of the examination region of the examination object.

In a further embodiment of the hybrid medical apparatus, the X-ray source may be arranged for movement along a fourth perimeter around the common spatial axis. The X-ray detector may further be arranged for movement along a fifth perimeter around the common spatial axis. In this case, the fourth perimeter and/or the fifth perimeter may be adaptable (e.g., with dynamic timing).

A plane of the fourth perimeter, in an operating state of the hybrid medical apparatus, may run in parallel to a plane of the fifth perimeter. With an elliptical embodiment of the fourth perimeter and/or of the fifth perimeter, a small and/or a large half axis of the fourth perimeter and/or of the fifth perimeter may be adaptable. For example, with a circular embodiment of the fourth perimeter and/or of the fifth perimeter, a radius may be adaptable.

For this, the X-ray source may be arranged by a first adjustable mounting apparatus on the third ring-shaped gantry for movement along the fourth perimeter. The X-ray detector may further be arranged by a second adjustable mounting apparatus on the fourth ring-shaped gantry for movement along the fifth perimeter. In this case, the fourth perimeter may be adapted by an adjustment and/or a movement of the X-ray source along the first adjustable mounting apparatus (e.g., at right angles to a plane of the fourth perimeter). In a similar way, the fifth perimeter may be adapted by an adjustment and/or a movement of the X-ray detector along the second adjustable mounting apparatus (e.g., at right angles to a plane of the fifth perimeter).

In this case, the adaptation of the fourth perimeter and of the fifth perimeter may be coordinated. The X-ray source and/or the X-ray detector may further, for example, be fastened tiltably and/or rotatably to the respective adjustable mounting apparatus such that the central beam always runs through the common isocenter.

This enables an opening angle of the double-cone-shaped sampling of the examination region of the examination object to be adapted (e.g., with dynamic timing).

In a further embodiment of the proposed hybrid medical apparatus, the imaging unit may have a first side and a second side in parallel to a plane of the first perimeter. In this case, the irradiation unit may be arranged on the first side, and a further irradiation unit may be arranged on the second side of the imaging unit for rotational movement in each case around a common spatial axis, with the common spatial axis running at right angles to the plane of the first perimeter. In this case, the further irradiation unit may be configured to carry out an irradiation of at least one part of the examination region of the examination object.

In this case, the further irradiation unit may, for example, have all characteristics of the irradiation unit. For example, the further irradiation unit may have a further ray source. The arrangement of the irradiation unit on the first side and the arrangement of the further irradiation unit on the second side enables an unimpeded and especially flexible alignment of the irradiation of the at least one part of the examination region of the examination object to be made possible. For example, the irradiation unit and/or the further irradiation unit may each be supported tiltably and/or rotatably. In this case, the irradiation may be undertaken from two different angulations (e.g., in a double-cone shape).

In a further embodiment of the hybrid medical apparatus, the irradiation unit and the further irradiation unit may be movable relative to one another in parallel to the common spatial axis.

This enables a dynamic adaptation of the respective angulation during the irradiation of the at least one part of the examination region of the examination object by the irradiation unit and the further irradiation unit to be able to be adapted (e.g., with dynamic timing).

In a further embodiment of the hybrid medical apparatus, the further irradiation unit may be arranged along a sixth perimeter for movement around the common spatial axis. The first perimeter and/or the sixth perimeter may further be adaptable (e.g., with dynamic timing).

In this case, the plane of the first perimeter, in an operating state of the hybrid medical apparatus, may run in parallel to a plane of the sixth perimeter. With an elliptical embodiment of the first perimeter and/or of the sixth perimeter, a small and/or a large half axis of the first perimeter and/or of the sixth perimeter may be adaptable. For example, with a circular embodiment of the first perimeter and/or of the sixth perimeter, a radius may be adaptable.

Moreover, the further irradiation unit (e.g., similarly to the irradiation unit) may have a fifth ring-shaped gantry. In this case, the ray source may be arranged by a third adjustable mounting apparatus on the first ring-shaped gantry for movement along the first perimeter. The further ray source may further be arranged by a third adjustable mounting apparatus on the fifth ring-shaped gantry for movement along the sixth perimeter. In this case, the first perimeter may be adapted by an adjustment and/or movement of the ray source along the third adjustable mounting apparatus (e.g., at right angles to the plane of the first perimeter). In a similar way, the sixth perimeter may be adapted by an adjustment and/or movement of the further ray source along the fourth adjustable mounting apparatus (e.g., at right angles to a plane of the sixth perimeter).

The ray source and/or the further ray source may, for example, further be fastened tiltably and/or rotatably to the respective adjustable mounting apparatus such that the central beam (e.g., during the irradiation of the at least one part of the examination region of the examination object) always runs through the common isocenter.

This enables an opening angle of the double-cone-shaped irradiation of the at least one part of the examination region of the examination object to be able to be adapted (e.g., with dynamic timing).

BRIEF DESCRIPTION OF THE DRAWINGS

In different figures, the same reference characters are used for the same features.

DETAILED DESCRIPTION

Figure 1:
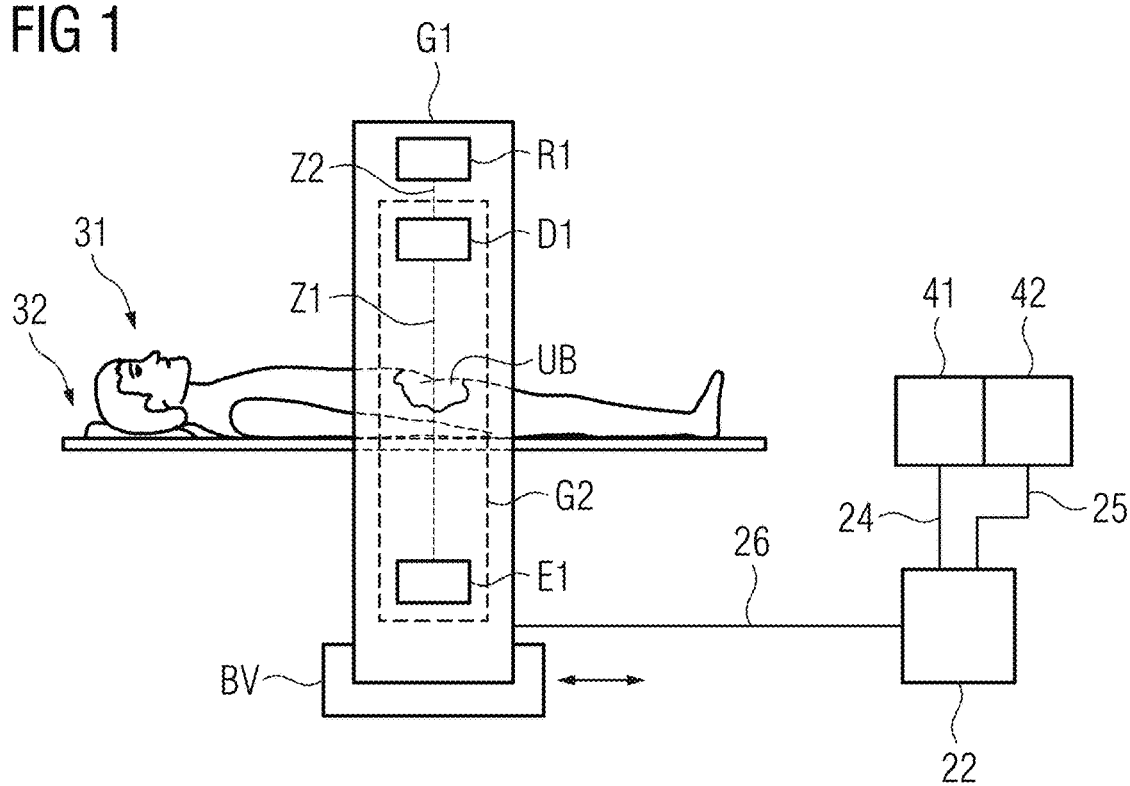
FIGS. 1 to 4 show schematic diagrams of different embodiments of a hybrid medical apparatus having two gantries.

FIG. 1 shows a schematic diagram of a form of embodiment of a proposed hybrid medical apparatus having an imaging unit, an irradiation unit, and a patient support apparatus 32. In this embodiment, the imaging unit may be configured to record image data of an examination region UB of an examination object 31 arranged on the patient support apparatus 32. The imaging unit may further have an X-ray source E1 and an X-ray detector D1. For recording of the image data, the X-ray source E1 may emit an X-ray fan beam. Further, the irradiation unit R1 may be configured to carry out an irradiation of at least one part of the examination region UB of the examination object 31. In this embodiment, the imaging unit and the irradiation unit R1 may have a common isocenter IZ. The irradiation unit R1 may further be arranged for rotational movement along a first perimeter independently of the imaging unit. Moreover, the X-ray source E1 and the X-ray detector D1 may be arranged for movement such that a central beam Z1 between the X-ray source E1 and the X-ray detector D1 runs through the common isocenter IZ. Further, the patient support apparatus 32 and/or the imaging unit and/or the irradiation unit R1 may be movable at least along a first spatial axis such that the examination region UB of the examination object is arrangeable in the common isocenter IZ.

The irradiation unit R1 may have a ray source that is configured for emitting an ionizing radiation. In this case, the ionizing radiation may be suitable for tumor therapy and/or for killing tumor cells. The ionizing radiation may further include X-ray radiation and/or Gamma radiation and/or particle radiation (e.g., electron radiation and/or proton radiation and/or ion radiation). In this case, the irradiation unit R1 (e.g., the ray source) may be able to be moved along the first perimeter such that the ionizing radiation is alignable to a center of the irradiation within the examination region UB of the examination object 31. In this case, the center of the irradiation may correspond to the common isocenter IZ. In this case, a central beam Z2 of the irradiation unit R1 (e.g., of the ray source) may run through the common isocenter IZ. The first perimeter may be embodied elliptical (e.g., circular). In one embodiment, the irradiation unit R1 (e.g., the ray source) may be movable along the first perimeter such that tissue adjoining the examination region UB of the examination object 31 is not irradiated with the ionizing radiation.

The irradiation unit R1 may have a ring-shaped first gantry G1, for example, where examination object 31 is arrangeable in an opening of the first gantry G1. In this case, the ring-shaped first gantry G1 may have an elliptical (e.g., circular) course. The ray source of the irradiation unit R1 may further be movable along the first spatial axis (e.g., relative to the patient support apparatus 32 and/or to the examination object 31 arranged thereon).

The imaging unit may further have a ring-shaped second gantry G2, where the examination object 31 arranged on the patient support apparatus 32 is arrangeable in an opening of the second gantry G2. In this case, the X-ray source E1 and the X-ray detector D1 may be arranged for movement along a second perimeter. Irradiation of the at least one part of the examination region UB of the examination object 31 may be undertaken by the irradiation unit R1 as a function of a positioning of the imaging unit (e.g., of the X-ray source E1 and/or of the X-ray detector D1). Moreover, the ring-shaped second gantry G2 may have an elliptical (e.g., circular) course. The imaging unit may further be movable along the first spatial axis (e.g., relative to the patient support apparatus 32 and/or to the examination object 31 arranged thereon).

In this case, the second gantry G2 may be arranged at least partly within the first gantry G1. In one embodiment, the first gantry G1 and the second gantry G2 are movable at least along the first spatial axis relative to one another. In this case, the irradiation unit R1 and/or the imaging unit and/or the patient support apparatus 32 may have a movement unit BV. In this case, the movement unit BV may include at least a wheel and/or a robot arm and/or a rail system and/or a hexapod.

In one embodiment, the proposed hybrid medical apparatus may make possible an irradiation and three-dimensional high-resolution slice imaging (e.g., simultaneously) of the examination region UB of the examination object 31. In this case, the examination object 31 may remain at rest on the patient support apparatus 32 during the irradiation and slice imaging.

In one embodiment, the hybrid medical apparatus may have a processing unit 22, a display unit 41 (e.g., a monitor and/or a display), and an input unit 42 (e.g., a keyboard). For recording the image data from the examination region UB of the examination object 31 to be imaged, the processing unit 22 may send a signal 26 to the X-ray source E1. Subsequently, the X-ray source E1 may emit the X-ray fan beam. When the X-ray fan beam, after an interaction with the examination region UB of the examination object 31 to be imaged, strikes a surface of the X-ray detector D1, the X-ray detector D1 may send a signal 26 to the processing unit 22. In one embodiment, the X-ray detector D1 may be embodied as a row detector (e.g., as a multi-row detector). The processing unit 22 may receive image data with the aid of the signal 26, for example.

The input unit 42 may be integrated into the display unit 41 (e.g., with a capacitive input display). In this case, an input of an operator at the input unit 42 may make it possible to control the hybrid medical apparatus (e.g., of the imaging unit and/or of the irradiation unit R1 and/or of the patient support apparatus 32 and/or of the movement unit BV). For this, the input unit 42 may send a signal 25 to the processing unit 22, for example.

The display unit 41 may further be configured to display information and/or graphic displays of information of the hybrid medical apparatus and/or of the processing unit 22 and/or of further components. For this, the processing unit 22 may send a signal 24 to the display unit 41, for example. For example, the display unit 41 may be configured to display a graphical display of the image data.

Figure 2:
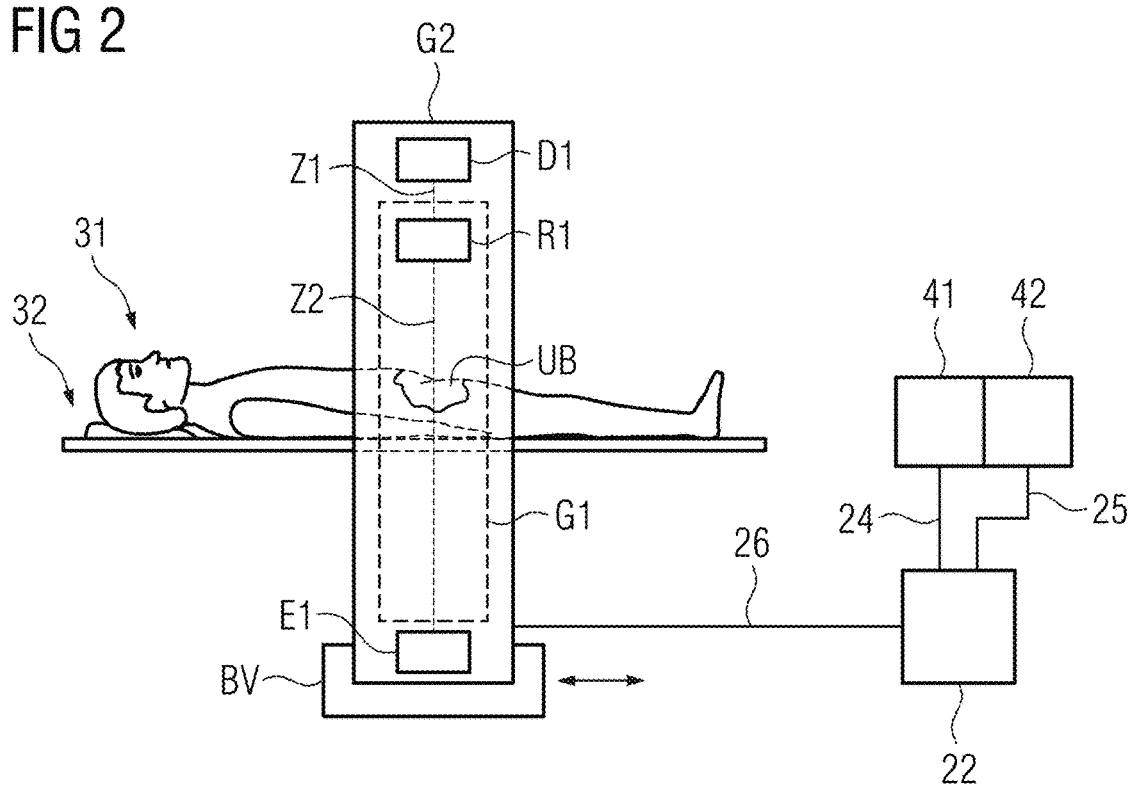
Figure 3:
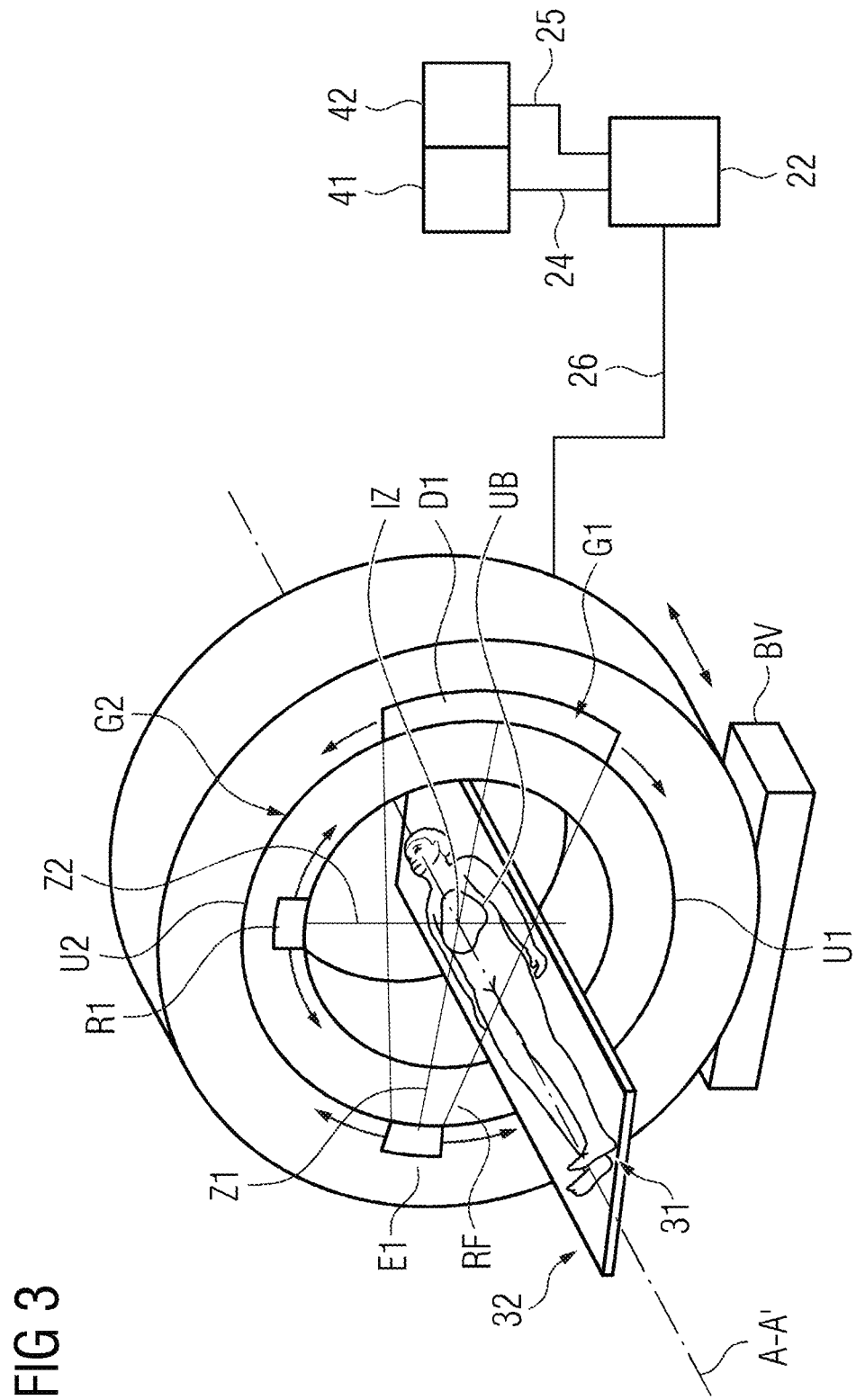

In the form of embodiment shown schematically in FIGS. 2 and 3, the first gantry G1 may be arranged at least partly within the second gantry G2.

In this case, the X-ray source E1 and the X-ray detector D1 are arranged for movement along a second perimeter U2. The image data from the examination region UB of the examination object 31 may further be recorded as a function of a positioning of the irradiation unit R1. For example, the imaging unit and/or the irradiation unit R1 and/or the patient support apparatus 32 and/or an arrangement of these components may be movable translationally at least along the common spatial axis A-A' by the movement unit BV.

Figure 4:
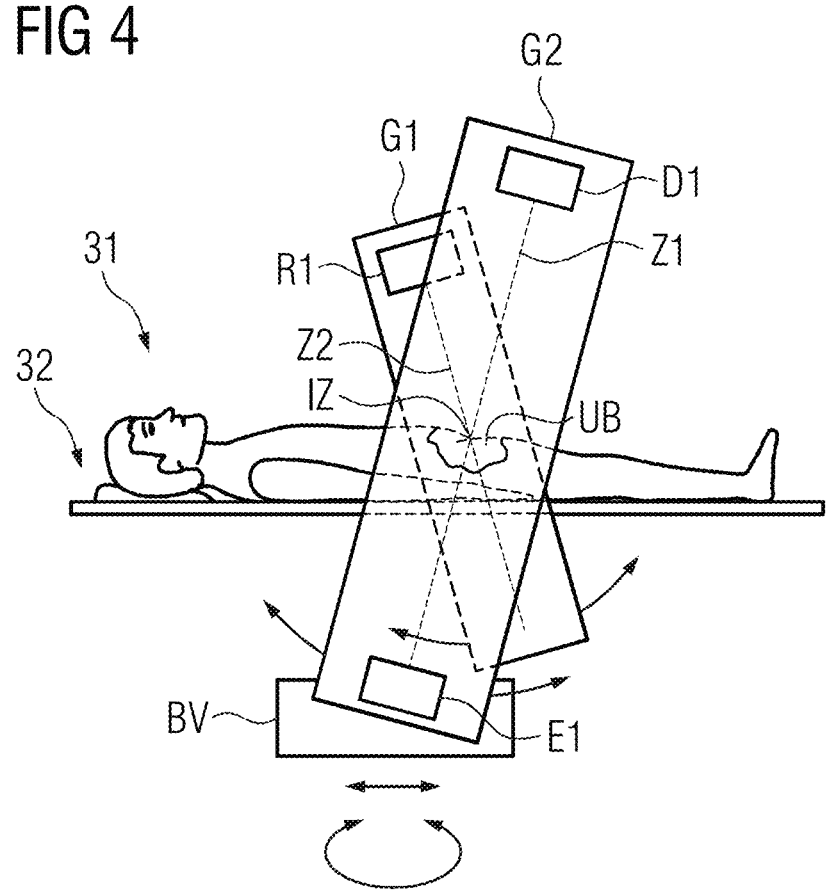

FIG. 4 shows a schematic diagram of a further form of embodiment of the proposed hybrid medical apparatus. In this case, the imaging unit (e.g., the second gantry G2) may be movable tiltably and/or translationally relative to the irradiation unit R1 (e.g., to the first gantry G1). The irradiation unit R1 may further be movable tiltably and/or translationally relative to the imaging unit. Moreover, the imaging unit and/or the irradiation unit R1 may be movable tiltably and/or translationally relative to the patient support apparatus 32 (e.g., to the examination object 31 arranged on the patient support apparatus 32). Further, the imaging unit and the irradiation unit R1 may be movable tiltably and/or translationally in a fixed arrangement to one another relative to the examination object 31. In this case, the imaging unit and/or the irradiation unit R1 may be supported tiltably by the movement unit BV (e.g., including a hexapod; around the common isocenter IZ). In this case, the movement unit BV may have at least one hexapod for movable support of the imaging unit and/or of the irradiation unit R1. The movement unit BV may further make possible a rotational movement of the first gantry G1 and/or of the second gantry G2 around a vertical spatial axis.

Figure 5:
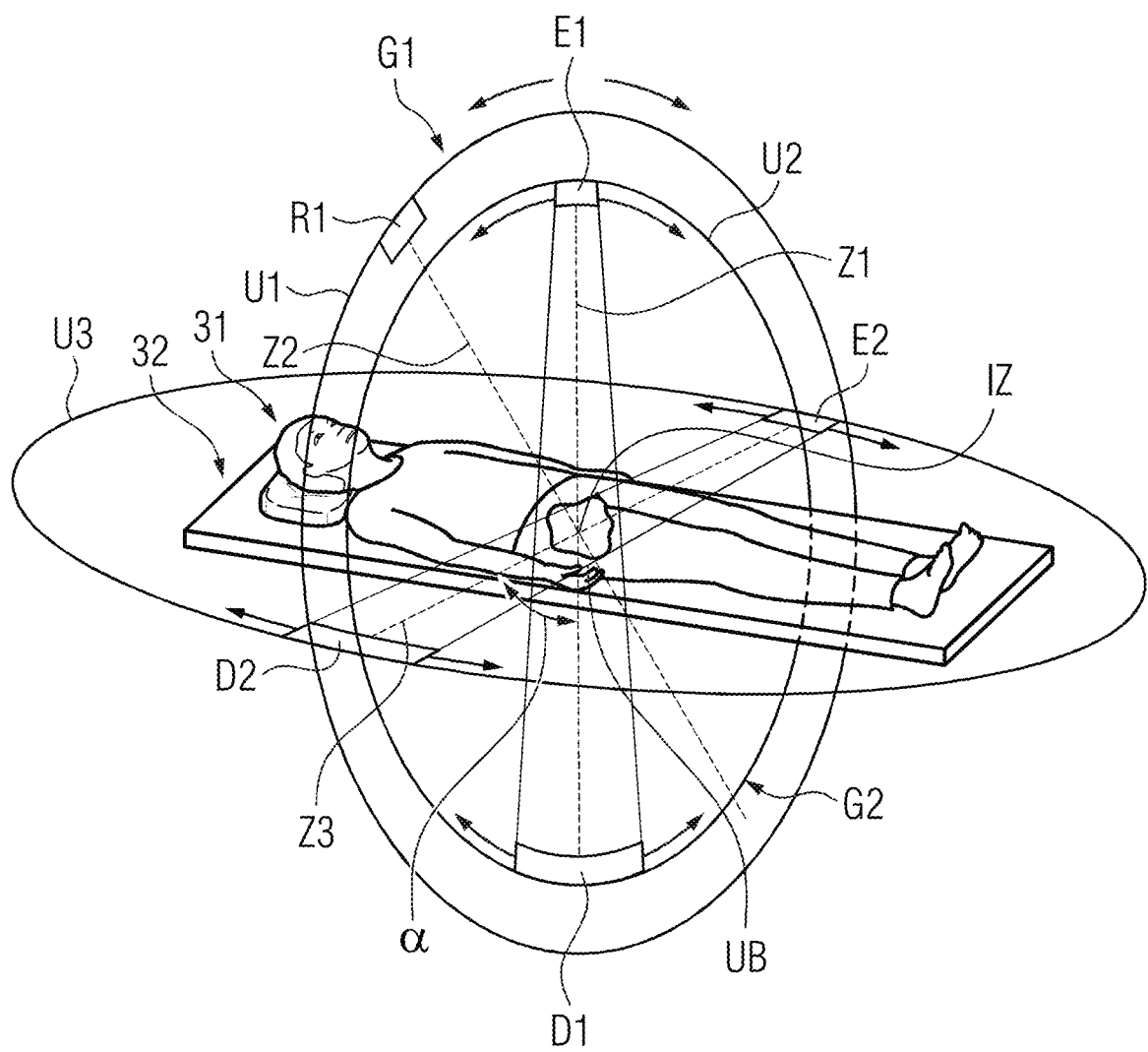
FIG. 5 shows a schematic diagram of an embodiment of the hybrid medical apparatus, where an imaging unit is configured as a biplanar X-ray device.

Shown schematically in FIG. 5 is a further form of embodiment of the proposed hybrid medical apparatus. In this case, the imaging unit may have a further X-ray source E2 and a further X-ray detector D2. In this case, the further X-ray source E2 and the further X-ray detector D2 may be arranged for movement in each case around the common isocenter IZ such that, in an operating state of the hybrid medical apparatus, a further central beam Z3 runs through the common isocenter IZ between the further X-ray source E2 and the further X-ray detector D2 at a predetermined angle α in relation to the central beam Z1 (e.g., 90°). For this, the further X-ray source E2 and the further X-ray detector D2 may be arranged for movement along a further gantry and/or along a C-arm. For example, the further X-ray source E2 and the further X-ray detector D2 may be movable along a third perimeter U3 around the common isocenter IZ. The further gantry and/or the C-arm may be fastened movably to the imaging unit and/or the irradiation unit and/or the movement unit BV.

The further X-ray source E2 may further be configured for emitting at least one further X-ray fan beam. In one embodiment, the further X-ray detector D2 may be configured as a row detector (e.g., as a multi-row detector). In this case, the further X-ray detector D2 may further be configured, when struck by the at least one further X-ray fan beam, after an interaction with the examination region UB of the examination object 31 to be imaged, to provide a further signal to the processing unit 22.

This advantageously enables a biplanar imaging of the examination region UB of the examination object 31 by the imaging unit to be made possible.

Figure 6:
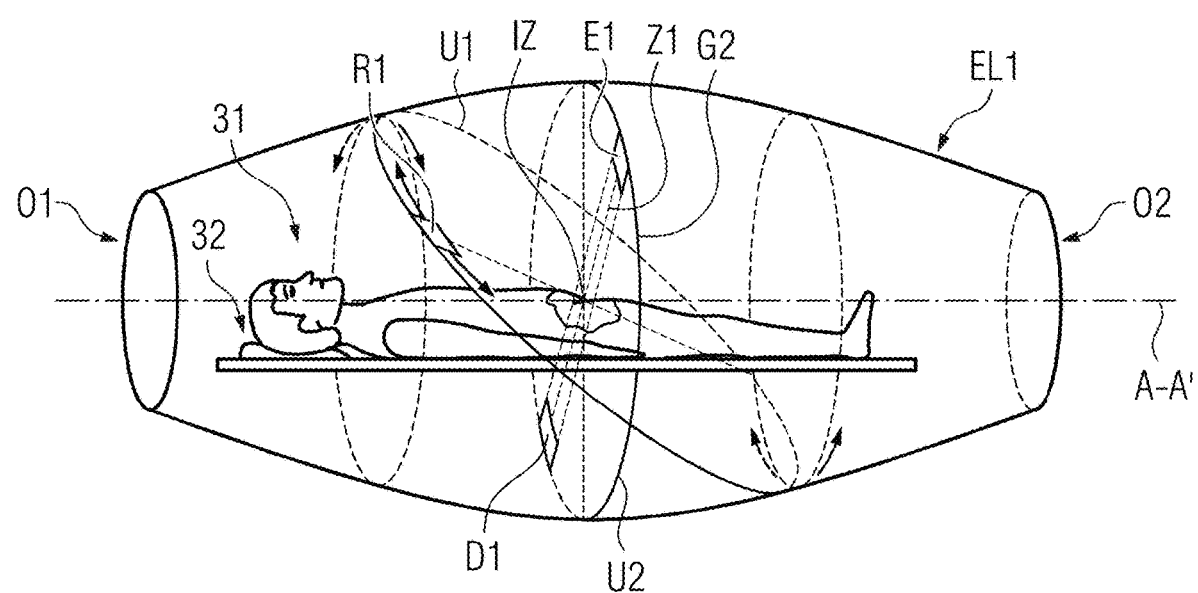
FIGS. 6 and 7 show schematic diagrams of different embodiments of the hybrid medical apparatus, where a plane of a first perimeter and/or a plane of a second perimeter is movable around the common isocenter.

Shown schematically in FIG. 6 is a further form of embodiment of the proposed hybrid medical apparatus. In this case, the imaging unit may have the second gantry G2, where the X-ray source E1 and the X-ray detector D1 are arranged for movement along the second perimeter U2. The irradiation unit R1 (e.g., the ray source) may further be arranged for movement along the first perimeter U1. In this case, a plane of the first perimeter U1 may be different than a plane of the second perimeter U2 in an operating state of the hybrid medical apparatus. For example, the plane of the first perimeter U1, in an operating state of the hybrid medical apparatus, may be movable around the common isocenter IZ (e.g., around the common spatial axis A-A'). In this case, the irradiation unit R1 may be arranged for movement on a first ellipsoid EL1 around the common isocenter IZ. For example, the first ellipsoid EL1 may be determined by the rotation of the first perimeter U1 around the common isocenter IZ (e.g., around the common spatial axis A-A').

Figure 7:
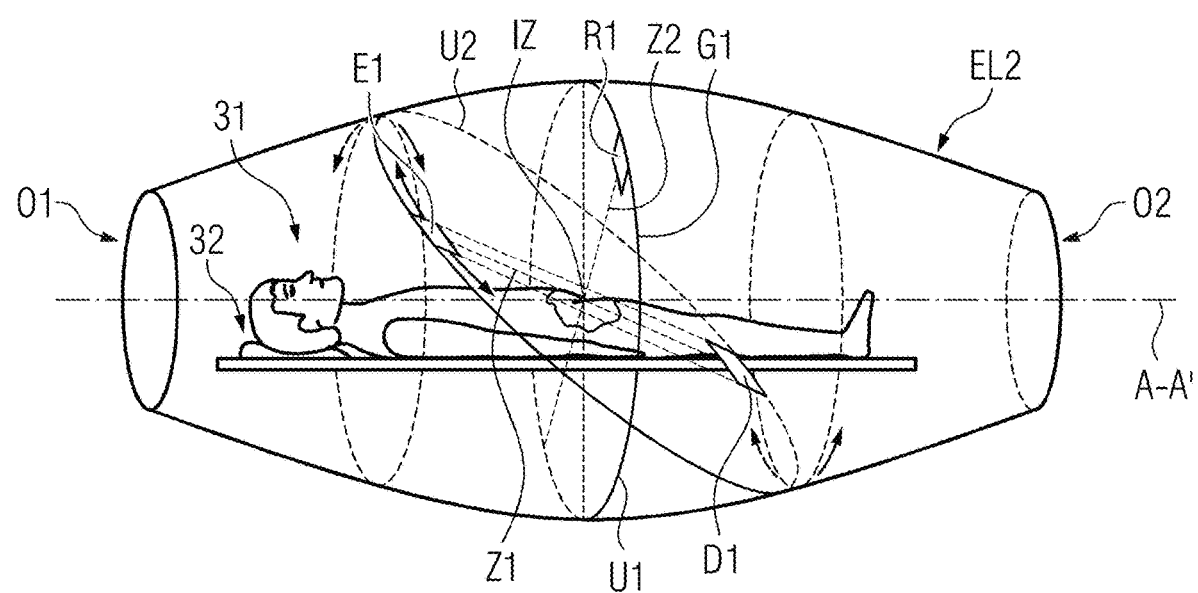

FIG. 7 shows a schematic diagram of a further form of embodiment of the proposed hybrid medical apparatus. In this case, the irradiation unit may have the first gantry G1, where the irradiation unit R1 (e.g., the ray source) is arranged for movement along the first perimeter U1. The imaging unit (e.g., the X-ray source E1 and the X-ray detector D1) may further be arranged for movement along the second perimeter U2. In this case, a plane of the second perimeter U2 may be different from a plane of the first perimeter U1 in an operating state of the hybrid medical apparatus. For example, the plane of the second perimeter U2, in an operating state of the hybrid medical apparatus, may be movable around the common isocenter IZ (e.g., around the common spatial axis A-A'). In this case, the X-ray source E1 and the X-ray detector D1 may be arranged for movement on a second ellipsoid EL2 around the common isocenter IZ. For example, the second ellipsoid EL2 may be determined by the rotation of the second perimeter U2 around the common isocenter IZ (e.g., around the common spatial axis A-A').

Figure 8:
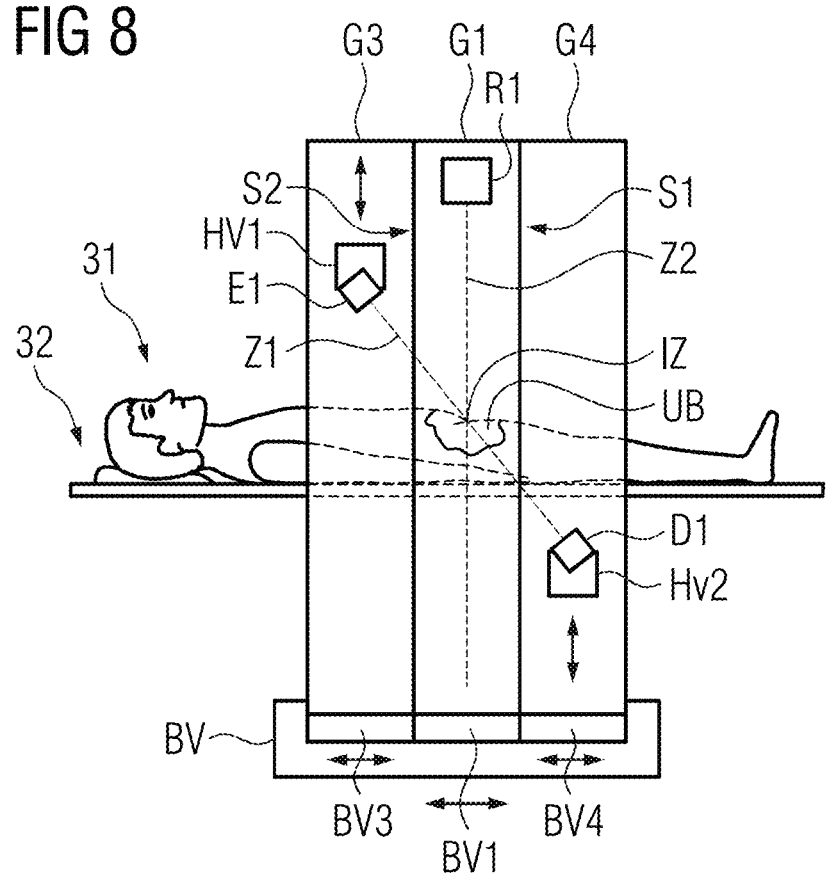
FIGS. 8 to 11 show schematic diagrams of different embodiments of the hybrid medical apparatus, where the imaging unit and/or an irradiation unit is movable along an ellipsoid.
Figure 9:
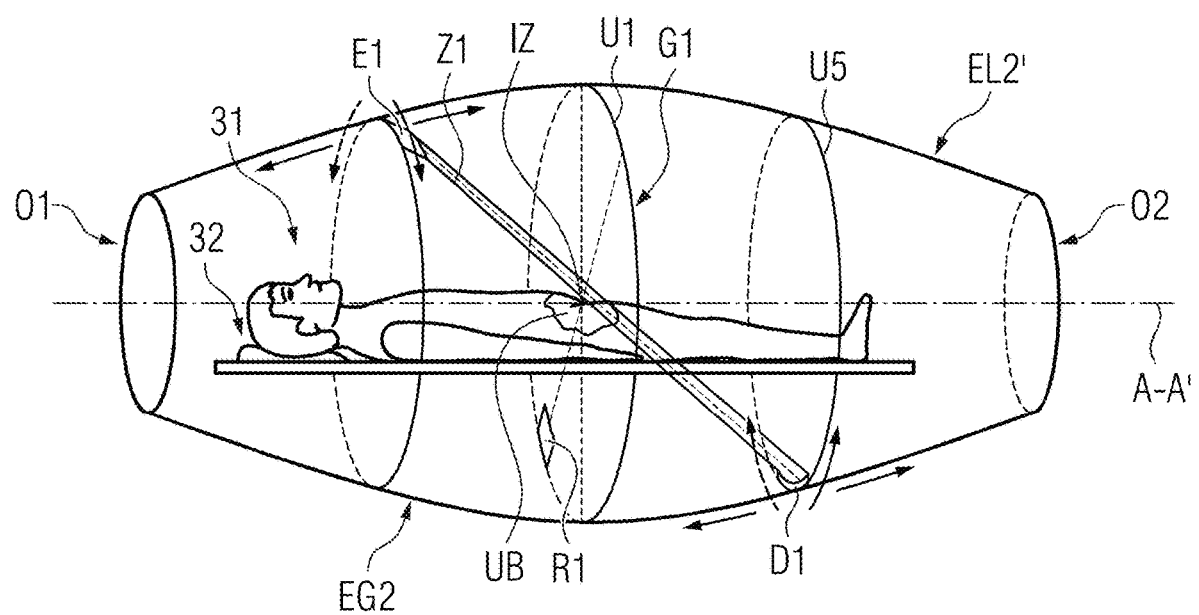

FIGS. 8 and 9 show different schematic diagrams of a further form of embodiment of the proposed hybrid medical apparatus. In this case, the irradiation unit R1 may have a first side S1 and a second side S2 in parallel to the plane of the first perimeter U1. The X-ray detector D1 on the first side S1 and the X-ray source E1 may be arranged on the second side S2 of the irradiation unit R1 in each case for rotational movement around the common spatial axis A-A'. In this case, the common spatial axis A-A' may run at right angles to the plane of the first perimeter U1. Moreover, the X-ray source E1 and the X-ray detector D1 may be movable in parallel to the common spatial axis A-A' relative to one another.

In one embodiment, the X-ray source E1 may be arranged along a fourth perimeter U4 for movement around the common spatial axis A-A'. In this case, the X-ray detector D1 may be arranged along a fifth perimeter U5 for movement around the common spatial axis A-A'. Moreover, the fourth U4 and/or the fifth perimeter U5 may be adaptable (e.g., with dynamic timing).

For this, the X-ray source E1 may be arranged by a first adjustable mounting apparatus HV1 on a third ring-shaped gantry G3 for movement along the fourth perimeter U4. The X-ray detector D1 may further be arranged by a second adjustable mounting apparatus HV2 on the fourth ring-shaped gantry G4 for movement along the fifth perimeter U5. In this case, the fourth perimeter U4 may be adapted by an adjustment and/or movement of the X-ray source E1 along the first adjustable mounting apparatus HV1 (e.g., at right angles to a plane of the fourth perimeter U4). In a similar way, the fifth perimeter U5 may be adapted by an adjustment and/or movement of the X-ray detector D1 along the second adjustable mounting apparatus HV2 (e.g., at right angles to a plane of the fifth perimeter U5). The first gantry G1 may further have a first movement unit BV1, the third gantry G3 may further have a third movement unit BV3, and the fourth gantry G4 may further have a fourth movement unit BV4. In one embodiment, each of the movement units may make possible a translational movement of the respective gantry at least along the common spatial axis A-A'.

In this case, the adaptation of the fourth perimeter U4 and of the fifth perimeter U5 may be coordinated. The X-ray source E1 and/or the X-ray detector D1 may be fastened tiltably and/or rotatably to the respective adjustable mounting apparatus HV1 and HV2, such that the central beam Z1 always runs through the common isocenter IZ.

This enables an opening angle of a double-cone-shaped sampling of the examination region UB of the examination object 31 (e.g., to be able to be adapted with dynamic timing).

As shown in FIG. 9, the X-ray source E1 and the X-ray detector D1 may be arranged for movement along the second ellipsoid EL2'. In this case, a movement trajectory of the X-ray source E1 and of the X-ray detector D1 along the second ellipsoid EL2' (e.g., by a coordinated translational movement of the third gantry G3 and of the fourth gantry G4 along the common spatial axis A-A' and an adaptation of the fourth perimeter U4 and of the fifth perimeter U5 corresponding thereto) may be made possible.

As an alternative or in addition, the X-ray source E1 and the X-ray detector D1 may each be arranged for movement along a second common gantry EG2, which has the shape of the second ellipsoid EL2'. In this case, the second common gantry EG2 may have a first opening O1 and a second opening O2 (e.g., along the common spatial axis A-A') for accepting the examination object 31 and the patient support apparatus 32.

Figure 10:
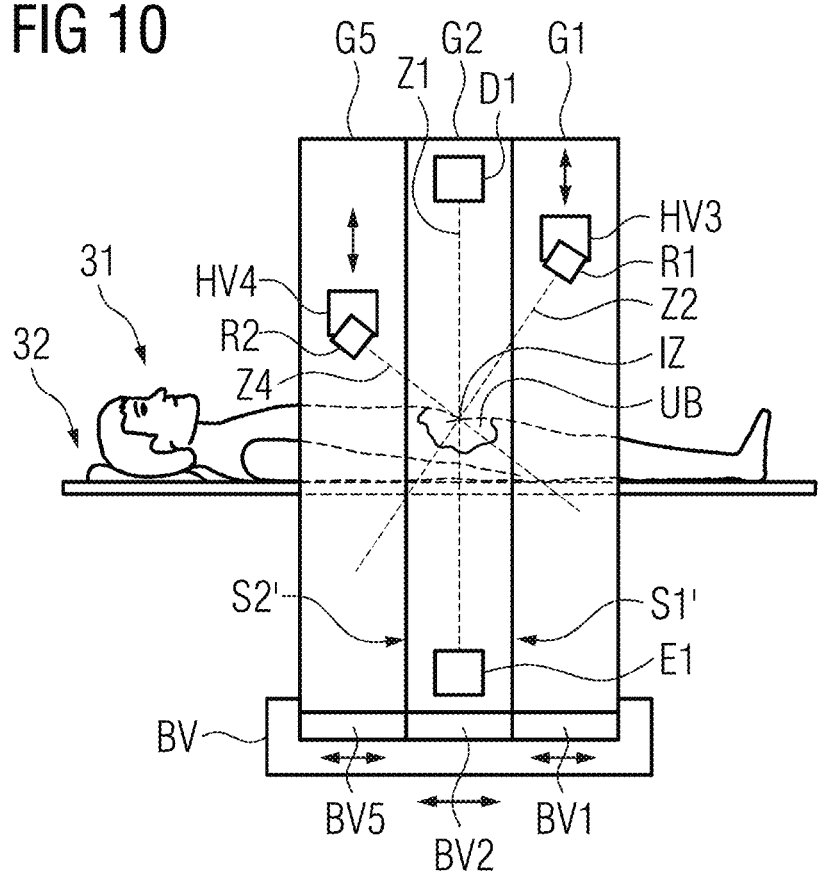
Figure 11:
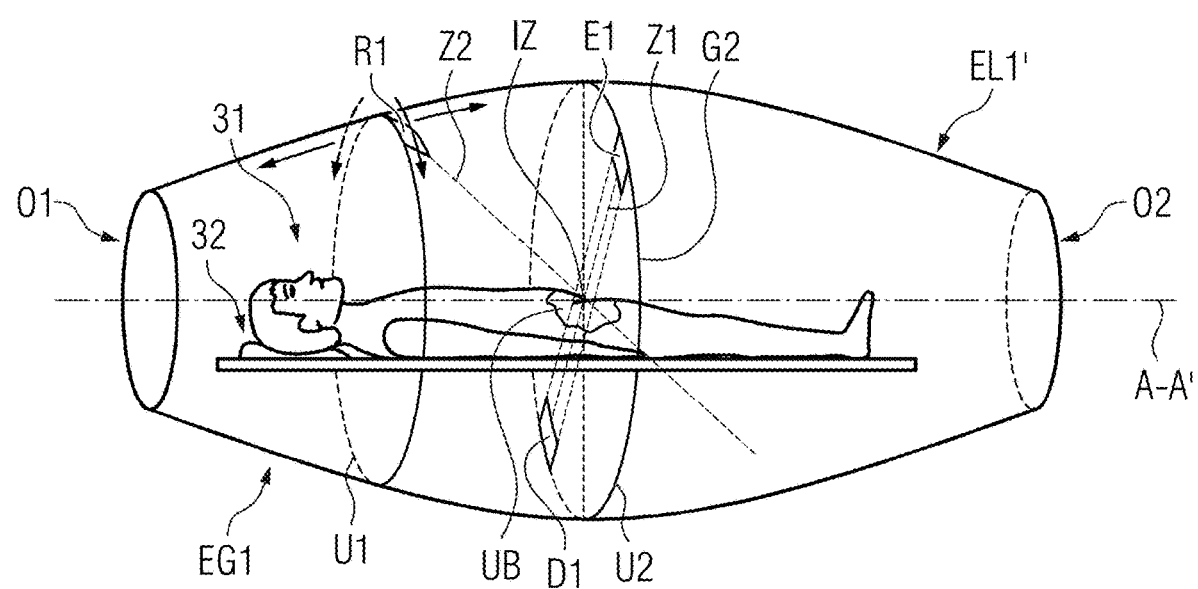

FIGS. 10 and 11 show different schematic diagrams of a further form of embodiment of the proposed hybrid medical apparatus. In this case, the imaging unit may have a first side S1 and a second side S2 in parallel to a plane of the first perimeter U1. The irradiation unit R1 may further be arranged on the first side S1', and a further irradiation unit R2 may be further arranged on the second side S2' of the imaging unit for rotational movement around the common spatial axis A-A' in each case, with the common spatial axis A-A' running at right angles to the plane of the first perimeter U1. In this case, the further irradiation unit R2 may be configured to carry out an irradiation of at least one part of the examination region UB of the examination object 31.

In one embodiment, the further X-ray source R2 may be arranged along a sixth perimeter U6 for movement around the common spatial axis A-A'. Moreover, the first perimeter U1 and/or the sixth perimeter U6 may be able to be adapted (e.g., with dynamic timing).

For this, the irradiation unit R1 (e.g., the ray source) may be arranged by a third adjustable mounting apparatus HV3 on the first ring-shaped gantry G1 for movement along the first perimeter U1. The further irradiation unit R2 (e.g., the further ray source) may further be arranged by a fourth adjustable mounting apparatus HV4 on a fifth ring-shaped gantry G5 for movement along the sixth perimeter U6. In this case, the first perimeter U1 may be adapted by an adjustment and/or movement of the irradiation unit R1 along the third adjustable mounting apparatus HV3 (e.g., at right angles to a plane of the first perimeter U1). In a similar way, the sixth perimeter U6 may be adapted by an adjustment and/or movement of the further irradiation unit R2 along the fourth adjustable mounting apparatus HV4 (e.g., at right angles to a plane of the sixth perimeter U6). The first gantry G1 may further have a first movement unit BV1, the second gantry G2 may further have a second movement unit BV2, and the fifth gantry G5 may further have a fifth movement unit BV5. In one embodiment, each of the movement units may make a translational movement of the respective gantry at least along the common spatial axis A-A' possible.

In this case, the adaptation of the first perimeter U1 and of the sixth perimeter U6 may be coordinated. The irradiation unit R1 and/or the further irradiation unit R2 may be fastened tiltably and/or rotatably to the respective adjustable mounting apparatus HV3 and HV4 such that the central beam Z2 and the central beam Z4 of the further irradiation unit R2 always runs through the common isocenter IZ.

Through this, an opening angle of a double-cone-shaped irradiation of the examination region UB of the examination object 31 may be adaptable (e.g., with dynamic timing).

As shown in FIG. 11, the irradiation unit R1 may be arranged for movement along the first ellipsoid EL1'. In this case, a movement trajectory of the irradiation unit R1 along the second ellipsoid EL2' may be made possible by a coordinated translational movement of the first gantry G1 along the common spatial axis A-A' and an adaptation of the first perimeter U1 corresponding thereto, for example. In addition, the further irradiation unit R2 (not shown here) may be arranged for movement along the first ellipsoid EL1'. In this case, a movement trajectory of the further irradiation unit R2 along the second ellipsoid EL2' may be made possible by a coordinated translational movement of the fifth gantry G5 along the common spatial axis A-A' and an adaptation of the sixth perimeter U6 corresponding thereto, for example.

As an alternative or in addition, the irradiation unit R1 and the further irradiation unit R2 (not shown here) may each be arranged for movement along a first common gantry EG1, which has the shape of the first ellipsoid EL1'. In this case, the first common gantry EG1 may have a first opening O1 and a second opening O2 (e.g., along the common spatial axis A-A') for accepting the examination object 31 and the patient support apparatus 32.

A combination of the forms of embodiment of the proposed hybrid medical apparatus shown in FIGS. 8 to 11 is also possible. In this case, the first ellipsoid EL1' and the second ellipsoid EL2' may be at least partly nested interdependently. In this case, at least one of the ellipsoids EL1' or EL2' may have larger half axes than the other ellipsoid.

The schematic diagrams described in the figures do not show any scale or proportion.

The method described in detail above as well as the apparatus shown merely involve exemplary embodiments that may be modified by the person skilled in the art in a wide variety of ways, without departing from the scope of the invention. Further, the use of the indefinite article "a" or "an" does not exclude the features concerned also being able to be present more than once. Likewise, the terms "unit" and "element" do not exclude the components concerned consisting of multiple interoperating subcomponents, which, where necessary, may also be spatially distributed.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A hybrid medical apparatus comprising:
   an imaging unit;
   an irradiation unit; and
   a patient support apparatus,
   wherein the imaging unit is configured to record image data of an examination region of an examination object arranged on the patient support apparatus,
   wherein the irradiation unit is configured to carry out an irradiation of at least one part of the examination region of the examination object, wherein the imaging unit and the irradiation unit have a common isocenter, wherein the irradiation unit is arranged for rotational movement along a first perimeter independently of the imaging unit, wherein the imaging unit comprises an X-ray source and an X-ray detector, wherein the X-ray source and the X-ray detector are arranged for movement such that a central beam between the X-ray source and the X-ray detector runs through the common isocenter, wherein the X-ray source is configured to emit an X-ray fan beam for recording of the image data, wherein the patient support apparatus, the imaging unit, the irradiation unit, or any combination thereof is movable at least along a first spatial axis such that the examination region of the examination object is arrangeable in the common isocenter, wherein the X-ray detector is configured as a row detector, wherein the X-ray source and the X-ray detector are arranged for movement along a second perimeter, the second perimeter being inside the first perimeter, and wherein the irradiation by the irradiation unit is undertaken as a function of a positioning of the imaging unit, the recording of the image data from the examination region of the examination object is undertaken as a function of a positioning of the irradiation unit, or a combination thereof.

2. The hybrid medical apparatus of claim 1, wherein the imaging unit further comprises another X-ray source and another X-ray detector, wherein the other X-ray source and the other X-ray detector are arranged for movement around the common isocenter in each case such that, in an operating state of the hybrid medical apparatus, another central beam between the other X-ray source and the other X-ray detector runs at a predetermined angle in relation to the central beam through the common isocenter.

3. The hybrid medical apparatus of claim 1, wherein the imaging unit, the irradiation unit, or the imaging unit and the irradiation unit are movable tiltably, translationally, or tiltably and translationally.

4. The hybrid medical apparatus of claim 1, wherein, in an operating state of the hybrid medical apparatus, a plane of the first perimeter is different than a plane of the second perimeter.

5. The hybrid medical apparatus of claim 4, wherein the plane of the first perimeter, in an operating state of the hybrid medical apparatus, is movable around the common isocenter, and wherein the irradiation unit is arranged on a first ellipsoid for movement around the common isocenter.

6. The hybrid medical apparatus of claim 4, wherein the plane of the second perimeter, in an operating state of the hybrid medical apparatus, is movable around the common isocenter, and wherein the X-ray detector and the X-ray source are arranged on a second ellipsoid for movement around the isocenter.

7. The hybrid medical apparatus of claim 1, wherein the irradiation unit has a first side and a second side in parallel to a plane of the first perimeter, wherein the X-ray detector is arranged on the first side, and the X-ray source is arranged on the second side of the irradiation unit for rotational movement in each case around a common spatial axis, with the common spatial axis running at right angles to the plane of the first perimeter.

8. The hybrid medical apparatus of claim 7, wherein the X-ray source and the X-ray detector are movable relative to each other in parallel to the common spatial axis.

9. The hybrid medical apparatus of claim 7, wherein the X-ray source is arranged for movement along a second perimeter around the common spatial axis, wherein the X-ray detector is arranged for movement along a third perimeter around the common spatial axis, and wherein the second perimeter, the third perimeter, or the second perimeter and the third perimeter are adaptable.

10. The hybrid medical apparatus of claim 9, wherein the second perimeter, the third perimeter, or the second perimeter and the third perimeter are adaptable with dynamic timing.

11. The hybrid medical apparatus of claim 1, wherein the imaging unit has a first and a second side in parallel to a plane of the first perimeter, wherein the irradiation unit on the first side and another irradiation unit on the second side of the imaging unit are arranged for rotational movement around a common spatial axis in each case, with the common spatial axis running at right angles to the plane of the first perimeter, and wherein the other irradiation unit is configured to carry out an irradiation of at least one part of the examination region of the examination object.

12. The hybrid medical apparatus of claim 11, wherein the irradiation unit and the other irradiation unit are movable relative to one another in parallel to the common spatial axis.

13. The hybrid medical apparatus of claim 11, wherein the other irradiation unit is arranged along a fourth perimeter for movement around the common spatial axis, and wherein the first perimeter, the fourth perimeter, or the first perimeter and the fourth perimeter are adaptable.

14. The hybrid medical apparatus of claim 13, wherein the first perimeter, the fourth perimeter, or the first perimeter and the fourth perimeter are adaptable with dynamic timing.

15. A hybrid medical apparatus comprising:
an imaging unit;
an irradiation unit; and
a patient support apparatus, wherein the imaging unit is configured to record image data of an examination region of an examination object arranged on the patient support apparatus, wherein the irradiation unit is configured to carry out an irradiation of at least one part of the examination region of the examination object, wherein the imaging unit and the irradiation unit have a common isocenter, wherein the irradiation unit is arranged for rotational movement along a first perimeter independently of the imaging unit, wherein the imaging unit comprises an X-ray source and an X-ray detector, wherein the X-ray source and the X-ray detector are arranged for movement such that a central beam between the X-ray source and the X-ray detector runs through the common isocenter, wherein the X-ray source is configured to emit an X-ray fan beam for recording of the image data, wherein the patient support apparatus, the imaging unit, the irradiation unit, or any combination thereof is movable at least along a first spatial axis such that the examination region of the examination object is arrangeable in the common isocenter, wherein the X-ray source and the X-ray detector are arranged for movement along a second perimeter, the second perimeter being inside the first perimeter, and wherein the irradiation by the irradiation unit is undertaken as a function of a positioning of the imaging unit, the recording of the image data from the examination region of the examination object is undertaken as a function of a positioning of the irradiation unit, or a combination thereof.

16. A hybrid medical apparatus comprising:
an imaging unit;
an irradiation unit; and
a patient support apparatus,
wherein the imaging unit is configured to record image data of an examination region of an examination object arranged on the patient support apparatus,
wherein the irradiation unit is configured to carry out an irradiation of at least one part of the examination region of the examination object,
wherein the imaging unit and the irradiation unit have a common isocenter,
wherein the irradiation unit is arranged for rotational movement along a first perimeter independently of the imaging unit,
wherein the imaging unit comprises an X-ray source and an X-ray detector,
wherein the X-ray source and the X-ray detector are arranged for movement such that a central beam between the X-ray source and the X-ray detector runs through the common isocenter,
wherein the X-ray source is configured to emit an X-ray fan beam for recording of the image data,
wherein the patient support apparatus, the imaging unit, the irradiation unit, or any combination thereof is movable at least along a first spatial axis such that the examination region of the examination object is arrangeable in the common isocenter,
wherein the imaging unit further comprises another X-ray source and another X-ray detector,
wherein the other X-ray source and the other X-ray detector are arranged for movement around the common isocenter in each case such that, in an operating state of the hybrid medical apparatus, another central beam between the other X-ray source and the other X-ray detector runs at a predetermined angle in relation to the central beam through the common isocenter,
wherein the X-ray source and the X-ray detector are arranged for movement along a second perimeter, and
wherein the further X-ray source and the further X-ray detector are arranged for movement along a third perimeter, wherein a plane of the third perimeter is arranged in an operating state of the hybrid medical apparatus intersecting a plane of the second perimeter.

* * * * *